United States Patent
Apert et al.

(10) Patent No.: US 9,241,890 B2
(45) Date of Patent: Jan. 26, 2016

(54) COSMETIC AND/OR DERMATOLOGICAL USE OF OLIGOSACCHARIDE COMPOUNDS FOR PREVENTING AND TREATING STRETCH MARKS

(75) Inventors: Laurent Apert, Dijon (FR); Marielle Bouschbacher, Chambolle-Musigny (FR)

(73) Assignees: SOCIETE DE DEVELOPPEMENT ET DE RECHERCHE INDUSTRIELLE, Chenove (FR); LABORATOIRES URGO, Chenove (FR)

( * ) Notice: Subject to any disclaimer, the term of this patent is extended or adjusted under 35 U.S.C. 154(b) by 0 days.

(21) Appl. No.: 14/131,794

(22) PCT Filed: Jul. 12, 2012

(86) PCT No.: PCT/FR2012/051669
§ 371 (c)(1),
(2), (4) Date: Jan. 9, 2014

(87) PCT Pub. No.: WO2013/007961
PCT Pub. Date: Jan. 17, 2013

(65) Prior Publication Data
US 2014/0155346 A1 Jun. 5, 2014

(30) Foreign Application Priority Data
Jul. 13, 2011 (FR) .................................... 11 56431

(51) Int. Cl.
*A61K 31/70* (2006.01)
*A61K 8/60* (2006.01)
*A61K 31/7016* (2006.01)
*A61K 45/06* (2006.01)
*A61Q 19/06* (2006.01)
*A61K 8/73* (2006.01)
*A61Q 19/00* (2006.01)

(52) U.S. Cl.
CPC . *A61K 8/60* (2013.01); *A61K 8/735* (2013.01); *A61K 31/7016* (2013.01); *A61K 45/06* (2013.01); *A61Q 19/00* (2013.01); *A61Q 19/06* (2013.01)

(58) Field of Classification Search
CPC ......... A61K 8/60; A61K 45/06; A61K 8/735; A61K 31/7016; A61K 31/702; A61Q 19/00
See application file for complete search history.

(56) References Cited

U.S. PATENT DOCUMENTS

| | | | | |
|---|---|---|---|---|
| 5,908,836 | A | * | 6/1999 | Bar-Shalom et al. ........... 514/53 |
| 5,911,980 | A | * | 6/1999 | Samour et al. ............. 424/70.17 |
| 2007/0048355 | A1 | * | 3/2007 | Perlman ....................... 424/443 |
| 2008/0299157 | A1 | * | 12/2008 | Fares et al. .................... 424/401 |

FOREIGN PATENT DOCUMENTS

| | | |
|---|---|---|
| BR | PI0902206 | 3/2011 |
| EP | 0415458 | 3/1991 |
| FR | 2784029 | 4/2000 |
| FR | 2824474 | 11/2002 |
| FR | 2916355 | 11/2008 |
| FR | 2953522 | 6/2011 |
| WO | 01/17486 | 3/2001 |
| WO | 02/089818 | 11/2002 |

OTHER PUBLICATIONS

International Search Report in PCT/FR2012/051669 dated Oct. 2, 2012.

* cited by examiner

*Primary Examiner* — Elli Peselev
(74) *Attorney, Agent, or Firm* — McAndrews, Held & Malloy Ltd.; Nabeela Rasheed

(57) ABSTRACT

The present invention relates to a topical composition, in particular a cosmetic and/or dermatological composition, to be used for preventing and/or treating stretch marks, including, in a physiologically acceptable medium, an effective amount of at least one synthetic polysulfated oligosaccharide having 1 to 4 glycose units, the salts thereof, and/or the derivatives thereof. The invention also relates to a cosmetic method, in particular for treating stretch marks, including at least one step of applying said composition to the skin.

21 Claims, No Drawings

COSMETIC AND/OR DERMATOLOGICAL USE OF OLIGOSACCHARIDE COMPOUNDS FOR PREVENTING AND TREATING STRETCH MARKS

The present application is filed pursuant to 35 U.S.C. 371 as a U.S. National Phase application of International Patent Application No. PCT/FR2012/051669, which was filed Jul. 12, 2012, claiming the benefit of priority to French Patent Application No. 1156431, which was filed on Jul. 13, 2011. The entire text of the aforementioned applications is incorporated herein by reference in its entirety.

The present invention relates to a topical composition, notably cosmetic and/or dermatological, useful for preventing and/or treating stretch marks, comprising, in a physiologically acceptable vehicle, an effective amount of at least one synthetic polysulfated oligosaccharide having 1 to 4 monosaccharide units, salts and/or derivatives thereof.

Stretch marks affect nearly 50% of the, mainly female, young population and despite partial spontaneous regression, they leave definite scars which age poorly.

Clinically, stretch marks present as linear or fusiform streaks like "strokes of the cane" from ½ cm to several centimeters long by 1 mm to 1 cm wide, symmetrical and multiple. Their surface can be smooth and taut, when they are recent, at the inflammatory stage, or crumpled, depressed, with an impression of emptiness to the touch and an appearance of the skin like crumpled cigarette paper, when they are old. Hairless, without sweat or sebaceous secretion, their color ranges from pink-red-purple to nacreous white. They appear more commonly in women than in men, and are located on the abdomen, the buttocks, the hips, the roots of the limbs, the breasts, or the shoulders.

They result from an abnormal distension of the skin occurring during certain conditions or episodes of life such as pregnancy or if very overweight. Stretch marks result from rupture of the collagen and elastin fibers in the deep layer of the dermis without any lesion of the epidermis being observed. Stretch marks differ from the "usual" scars that are the result of open wounds, burns or a pathology, since these wounds result from a lesion of the epidermis and of a part of the dermis of varying depth. The skin of an obese person, for example, is subjected to stretching that is directly proportional to the amount of fat stored in reserve. After losing weight, the skin does not regain its usual structure and remains stretched, distended. That is why stretch marks may appear in some obese subjects. They can also form on the limbs when bone growth has been particularly rapid. They are also a consequence of the inappropriate use of corticoids (cortisone), either in the form of ointment, or, most often, in injectable form. Stretch marks are also the result of excessive secretion of corticoid hormones (Cushing's disease). They can be scars of rounded shape occurring during secondary syphilis or typhoid. Weight-lifters are also likely to have stretch marks: this is so, moreover, for those engaging in some other sports.

At present there is not really any effective treatment for combating stretch marks. Massaging, derivatives of placenta extract, collagen creams, elastin creams, and silicon derivatives have not proved effective. Certain subjects may sometimes have recourse to surgery for removing an excessive amount of skin (excessive apron), but this intervention does not apply to stretch marks themselves.

There is therefore a constant need to find an effective solution for treating scars of this type.

Thus, European patent EP-B-1 784 205 describes the use of a botulinum toxin for making a medicinal product for treating stretch marks, where said botulinum toxin is intended to be administered to, or in the vicinity of, a patient's stretch marks. However, the use of a botulinum toxin is not recommended for certain subjects, for example pregnant women or subjects undergoing antibiotic treatment with aminoglycosides (Amiklin, Gentalline or streptomycin for example), recent anticoagulant treatment, recent anti-inflammatory treatment, or with known hypersensitivity to Botox®, myasthenia gravis, Lambert-Eaton syndrome. Moreover, injection, which is still a surgical procedure requiring qualified personnel, can pose risks of contamination.

Patent WO 02102348 relates to an anti-stretch mark product comprising a preparation intended for treating stretch marks on the skin, in a stick format, and a distributor receiving said preparation and comprising a distributing means that can be manipulated by a user and permits distribution of the preparation over the area required. However, the composition is complex, as is its manner of application.

Finally, French patent FR2857596 claims a special topical composition for the preventive treatment of stretch marks suitable for pregnant women, and containing a rich extract of lupeol.

There is at present a need for a new cosmetic composition having an action on stretch marks, which is effective.

Unexpectedly, the applicant found that the use of a particular synthetic polysulfated oligosaccharide compound allowed effective treatment of stretch marks.

The invention therefore relates to a cosmetic and/or dermatological composition, for use for preventing and/or treating stretch marks, comprising, in a physiologically acceptable vehicle, at least an effective amount of at least one of synthetic polysulfated oligosaccharide having 1 to 4 monosaccharide units, the salts and/or derivatives thereof.

In the sense of the present invention, synthetic polysulfated oligosaccharide means synthetic polymers formed from 1 to 4 monosaccharide units, and preferably 1 or 2 monosaccharide units, generally joined together by an alpha or beta glycosidic bond. In other words, they are mono-, di-, tri- or tetrasaccharides, and preferably mono- or disaccharides.

According to another of its aspects, the invention relates to a cosmetic procedure comprising at least one step in which a topical composition comprising at least an effective amount of at least one synthetic polysulfated oligosaccharide having from 1 to 4 monosaccharide units, salts and/or derivatives thereof is applied on the skin.

According to yet another of its aspects, the invention relates to the use of an effective amount of at least one synthetic polysulfated oligosaccharide having from 1 to 4 monosaccharide units, salts and/or derivatives thereof, together with an effective amount of at least one active substance, for manufacturing a cosmetic or dermatological composition intended for treating or preventing stretch marks.

"Cosmetic and/or dermatological composition" means, in the sense of the present application, a composition for topical application, comprising a cosmetically or dermatologically acceptable medium, i.e. which has a pleasant color, odor and feel, and does not cause unacceptable discomfort (tingling, tightness, redness), likely to put consumers off using this composition.

"Effective amount" means, in the sense of the present invention, a sufficient amount for obtaining the expected effect.

"Physiologically acceptable vehicle" denotes a nontoxic vehicle that can be applied on at least one keratinous material of human beings.

Synthetic Polysulfated Oligosaccharide

The composition according to the invention comprises at least one synthetic polysulfated oligosaccharide compound having from 1 to 4 monosaccharide units, salts and/or derivatives thereof.

The oligosaccharides used in the context of the present invention are synthetic oligomers formed from 1 to 4 monosaccharide units, and preferably from 1 or 2 monosaccharide units, generally joined together by an alpha or beta glycosidic bond. In other words, they are mono-, di-, tri- or tetrasaccharides, and preferably mono- or disaccharides.

There is no particular limitation regarding the nature of the monosaccharide units of these polysaccharides. Preferably, they will be pentoses or hexoses. As an example of monosaccharide, we may mention glucose, galactose or mannose. As an example of disaccharide, we may mention maltose, lactose, sucrose or trehalose. As an example of trisaccharide, we may mention melezitose. As an example of tetrasaccharide, we may mention stachyose.

Preferably, the oligosaccharide is a disaccharide, and more preferably sucrose.

"Polysulfated oligosaccharide" means, in the sense of the present application, an oligosaccharide of which at least two, and preferably all the hydroxyl groups of each monosaccharide have been substituted with a sulfate group.

Preferably, the polysulfated oligosaccharide used in the context of the present application is sucrose octasulfate.

The polysulfated oligosaccharides used in the context of the present invention can be in the form of salts or complexes.

As examples of salts, we may mention the alkali metal salts such as the sodium, calcium or potassium salts; silver salts; or the salts of amino acids.

As an example of complexes, we may mention the hydroxyaluminum complexes.

In the context of the present invention, compounds particularly preferred are as follows:
the potassium salt of sucrose octasulfate (KSOS);
the silver salt of sucrose octasulfate;
the hydroxyaluminum complex of sucrose octasulfate, commonly called sucralfate.

In particular, in the context of the present invention, the polysulfated oligosaccharides used are preferably the potassium salts rather than the aluminum salts of sucrose octasulfate.

The polysulfated oligosaccharides used in the context of the present invention can be in the form of micronized powder or in solubilized form.

Preferably, the polysulfated oligosaccharide preferred in the context of the present invention is the potassium salt of sucrose octasulfate (known by the abbreviation KSOS), marketed for example in the product Urgotul® Start as "NOSF" by URGO® Laboratories.

In particular, the synthetic polysulfated oligosaccharide compound is present in the composition according to the invention at a content between 0.1 and 50 wt %, relative to the total weight of the composition.

The synthetic polysulfated oligosaccharide compounds can be introduced, in the compositions according to the invention, alone or as a mixture of two or more of them, or else in combination with one (or more) other substance(s).

According to a particular embodiment of the invention, the composition comprises at least an amount of synthetic polysulfated oligosaccharides between 0.1 and 50 wt %, relative to the total weight of the composition.

According to a particular embodiment of the invention, the composition comprises at least an amount of synthetic polysulfated oligosaccharides such that the amount salted-out on the stretch mark is between 0.001 g/l and 50 g/l, and more preferably between 0.01 and 10 g/l.

Active Substance

Besides the synthetic polysulfated oligosaccharide compounds, the composition according to the invention can comprise one (or more) other active substance(s).

In general, the active substances are selected from antibacterial agents, antiseptics, antifungals, anti-inflammatories, active substances promoting healing and/or restructuring of the skin, antipruritics, UV filters, soothing agents, hydrating agents, depigmenting agents, keratolytic agents, antivirals, analgesics, anesthetics, vitamins and mixtures thereof.

In general, the active substances are selected from:
antibacterials such as Polymyxin B, the penicillins (amoxicillin), clavulanic acid, the tetracyclines, minocycline, chlortetracycline, the aminoglycosides, Amikacin, gentamicin, neomycin, silver and silver salts (sulfadiazine silver), probiotics;
antiseptics such as sodium mercurothiolate, eosin, chlorhexidine, phenylmercuric borate, hydrogen peroxide, Dakin solution, triclosan, biguanide, hexamidine, thymol, Lugol, iodinated povidone, merbromin, benzalkonium chloride and benzethonium chloride, ethanol, isopropanol, silver salts;
antifungals such as the polyenes, nystatin, amphotericin B, natamycin, the imidazoles (miconazole, ketoconazole, clotrimazole, econazole, bifonazole, butoconazole, fenticonazole, isoconazole, oxiconazole, sertaconazole, sulconazole, thiabendazole, tioconazole), the triazoles (fluconazole, itraconazole, ravuconazole, posaconazole, voriconazole), the allylamines, terbinafine, amorolfine, naftifine, butenafine;
flucytosine (antimetabolite), griseofulvin, caspofungin, micafungin, arginine;
anti-inflammatories such as the glucocorticoids, nonsteroidal anti-inflammatories, aspirin, ibuprofen, ketoprofen, flurbiprofen, diclofenac, aceclofenac, ketorolac, meloxicam, piroxicam, tenoxicam, naproxen, indometacin, naproxcinod, nimesulide, celecoxib, etoricoxib, parecoxib, rofecoxib, valdecoxib, phenylbutazone, niflumic acid, mefenamic acid;
active substances promoting healing and/or restructuring of the skin such as retinol, water-soluble vitamins such as vitamin A or derivatives thereof, vitamin E or derivatives thereof, N-acetyl-hydroxyproline, extracts of *Centella asiatica* and of dill, papain, the silicones, the essential oils of thyme, of niaouli, of rosemary and of sage, hyaluronic acid, allantoin, Héma'tîte® (Gattefossé), vitamin C, TEGO® Pep 4-17 (Evonik), Toniskin® (Silab), Collageneer® (Expanscience), Timecode® (Seppic), Gatuline® skin repair (Gattefossé), panthenol, PhytoCellTec° Alp Rose (MibelleBiochemistry), Serilesine® (Lipotec), heterosides of Talapetraka (Bayer), Stoichiol® (Codif), macarose (Sensient), Dermaveil (Ichimaru Pharcos), Phycosaccharide AI (Codif), metformin;
depigmenting agents such as kojic acid (KojicAcid SL®—Quimasso (Sino Lion)), arbutin (Olevatin®—Quimasso (Sino Lion)), mixture of sodium palmitoylpropyl and extract of white water lily (Sepicalm®—Seppic), undecylenoyl phenylalanine (Sepiwhite®—Seppic), extract of licorice obtained by fermentation of *Aspergillus* and ethoxydiglycol (GatulineWhitening®—Gattefossé), octadecenedioic acid (ODA White®—Sederma), alpha-arbutin (Alpha-arbutin®, SACI-CFPA (Pentapharm)), aqueous extract of leaves *Arctophylos Uva Ursi* (Melfade-J®—SACI-CFPA (Pentapharm)), the complex plant mixture Gigawhite® (SACI-CFPA (Alpaflor)), diacetylboldine (Lumiskin®—Sederma), extract of Japanese mandarin (Melaslow®—Sederma), mixture of extract of lemon enriched with citric acid and of extract of cucumber (Uninontan® U-34—Unipex), the mixture of extract of *Rumex occidentalis* and of vitamin C (Tyrostat® 11—Unipex), oligopeptides (Melanostatine 5®—Unipex), dipalmitatekojic (KAD-15®—Quimasso (Sino Lion)), the complex of natural origin Vegewhite® from LCW, wheat germ extracts (Clariskin® II—Silab), ethylenediamine tetraacetic acid (EDTA);

antipruritics such as hydrocortisone, enoxolone, diphenhydramine, the anti H1 antihistamines for local application;

UV filters such as Parsol MCX, Parsol 1789;

soothing agents such as chamomile, bisabolol, Zanthalene®, glycyrrhebenic acid, Tanactine® (CPN), Calmiskin® (Silab);

hydrating agents such as Xpermoist (Lipotec), hyaluronic acid, urea, fatty acids, glycerin, the waxes, Exossine® (Unipex);

keratolytic agents such as salicylic acid, zinc salicylate, ascorbic acid, the hydroxylated alpha acids (glycolic, lactic, malic, citric, tartaric acid), the extracts of silver maple, of morello cherry tree, of tamarind, urea, the topical retinoid Kératoline® (Sederma), the proteases obtained by fermentation of *Bacillus subtilis*, the product Linked-Papain® (SACI-CFPA), papain (proteolytic enzyme obtained from the papaya fruit);

vitamins such as retinol (vitamin A) and derivatives thereof, tocopherol (vitamin E) and derivatives thereof.

According to a preferred embodiment, the composition according to the invention comprises at least an effective amount of an active substance promoting healing and/or restructuring of the skin, preferably hyaluronic acid.

Moreover, the active substances according to the invention can be combined with active agents intended notably for preventing and/or treating skin disorders.

Pharmaceutical Form

The compositions according to the invention can be presented in all the pharmaceutical forms normally used by a person skilled in the art.

When the compositions are intended for topical administration, they can be in the form of solutions (aqueous, aqueous-alcoholic or oily), dispersions (of the lotion or serum type), emulsions of liquid or semiliquid consistency (of the milk type), suspensions or emulsions (of the cream type), aqueous or lipophilic gel, microemulsions, microcapsules, microparticles, or vesicular dispersions of the ionic and/or nonionic type. They can also be in the form of nonabsorbent interface dressings.

These compositions are prepared by the usual methods.

They can notably be in the form of creams for treatment or care of the face, for the great anatomical folds or for the body.

The compositions according to the invention can also consist of solid preparations such as soaps or cleansing bars.

Of course, the amount of synthetic polysulfated oligosaccharides used in the galenical formulation according to the invention is adapted in relation to the kinetics required as well as specific constraints connected with its nature, solubility, heat resistance, etc.

Generally, when it is used in a galenical formulation, the synthetic polysulfated oligosaccharide compound according to the invention can be incorporated at a content between 0.1 and 50 wt %, relative to the total weight of the formulation.

Water and Water-Soluble Solvents

According to a preferred embodiment, the composition of the invention can also comprise water, and notably a thermal and/or mineral water.

The composition according to the invention can also comprise one or more solvents miscible with water, such as the lower alcohols, notably ethanol and isopropanol, propylene glycol.

Fatty Phase

The composition according to the invention can also comprise a fatty phase.

When the composition of the invention is in the form of an emulsion, the proportion of the fatty phase can range from 5 to 80 wt %, and preferably from 5 to 50 wt %, relative to the total weight of the composition.

When the composition of the invention is a solution or an oily gel, the fatty phase can represent more than 90% of the total weight of the composition.

The oils used in the composition according to the invention are selected from those used conventionally in the cosmetic and/or dermatological field.

As fatty substances usable in the invention, we may mention, besides the unsaturated fatty acids, mineral oils, for example hydrogenated polyisobutene and liquid paraffin, vegetable oils, for example a liquid fraction of shea butter, sunflower oil, almond oil and apricot oil, animal oils for example perhydrosqualene, synthetic oils notably purcelline oil, isopropyl myristate and ethylhexyl palmitate, and fluorinated oils for example the perfluoropolyethers.

It is also possible to use fatty alcohols, fatty acids for example stearic acid and waxes notably paraffin wax, carnauba wax and beeswax.

It is also possible to use silicone compounds such as the silicone oils and for example the cyclomethicones and dimethicones, silicone waxes, resins and gums.

Emulsifiers

The composition according to the invention, when it is in the form of emulsion, can also comprise one or more emulsifiers and/or co-emulsifiers.

The emulsifiers and the co-emulsifiers used in the composition are selected from those used conventionally in the cosmetic and/or dermatological field.

As emulsifier usable in the invention, we may mention for example glycerol stearate, polysorbate 60, the mixture cetyl-stearyl alcohol/cetylstearyl alcohol ethoxylated with 33 moles of ethylene oxide sold under the name Sinnowax AO® by the company HENKEL, the mixture of PEG-6/PEG-32/Glycol Stearate sold under the name Tefose® 63 by the company GATTEFOSSE, PPG-3 myristyl ether, the silicone emulsifiers such as the cetyldimethicone copolyol and sorbitan mono- or tristearate, PEG-40 stearate, ethoxylated sorbitan monostearate (20OE).

The total content of emulsifiers and co-emulsifiers can notably range from 0.3 to 30 wt %, and preferably from 0.5 to 20 wt %, relative to the total weight of the composition.

Gelling Agents

The composition according to the invention can also comprise gelling agents.

As hydrophilic gelling agents, we may mention the carboxylic polymers such as the carbomers, the acrylic copolymers such as the acrylate/alkyl acrylate copolymers, the polyacrylamides and notably the mixture of polyacrylamide, C13-14-isoparaffin and Laureth-7 sold under the name Sepigel 305® by the company SEPPIC, the polysaccharides such as the cellulose derivatives such as the hydroxyalkylcelluloses and in particular hydroxypropylcellulose and hydroxyethylcellulose, the natural gums such as guar, carob, xanthan gum and the clays.

As lipophilic gelling agents, we may mention the modified clays such as bentones, the metal salts of fatty acids such as the aluminum stearates and hydrophobic silica, or else ethylcellulose and polyethylene.

Additives

The cosmetic and/or dermatological composition of the invention can also contain the additives that are usual in the cosmetic, pharmaceutical and/or dermatological field, such as preservatives, antioxidants, solvents, perfumes, fillers, odor absorbers and colorants. Depending on their nature, these additives can be added to the fatty phase and/or to the aqueous phase of the composition.

The amounts of these various additives are those used conventionally in the field considered, for example from 0.01 to 20% of the total weight of the composition.

Film

According to a preferred embodiment of the invention, the composition is in the form of a film, preferably a water-soluble polymer film of the filmogel® type.

"Film" means, according to the present invention, a thin solid.

"Thin" means a solid having a thickness of at most 1000 µm.

This film is grippable, i.e. it is generally of a suitable size to be easily manipulated by the user. It can be in the shape of a square, rectangle, disk or any other shape. A film generally has a thickness from 10 µm to 1000 µm, preferably from 20 to 500 µm and more preferably from 50 to 300 µm.

"Water-soluble film" means, in the sense of the present invention, a film that dissolves in water. It is a film consisting of one or more water-soluble or water-dispersible polymers, i.e. polymers having a solubility in water measured at 25° C. at least equal to 0.1 g/L (obtaining a solution that is macroscopically isotropic and transparent, colored or not). This solubility is preferably greater than or equal to 1 g/L.

The film according to the invention is preferably an "anhydrous film", i.e. a film comprising a water content below 15 wt %, preferably below 10 wt % and more preferably below 5 wt %, relative to the total weight of the film. More preferably, the film according to the invention is free from water.

The polymers that can be used for constituting these films can be of synthetic or natural origin, and, if necessary, modified by chemical reactions. They can be film-forming or non-film-forming. They are advantageously film-forming.

These polymers must be physiologically acceptable, i.e. compatible with the skin, the mucosae, the hair and the scalp.

The composition in the form of film notably comprises at least one film-forming polymer.

"Film-forming polymer" means a polymer that is able to form, on its own or in the presence of an auxiliary filming agent, a continuous film, and preferably a film whose cohesion and mechanical properties are such that said film can be isolated from a substrate.

These polymers are listed in the section "Film Formers" in the "International Cosmetic Ingredient Dictionary and Handbook" (see for example pages 2903 to 2906 of the ninth edition—2002).

The film-forming polymers can be selected for example from:

the vinyl polymers such as polyvinyl acetate, the polyvinylpyrrolidones, the copolymers of methylvinyl ether and maleic anhydride, the copolymer of vinyl acetate and crotonic acid, the copolymers of vinylpyrrolidone and vinyl acetate, the copolymers of vinylpyrrolidone and caprolactam, the polyvinyl alcohols. Preferably, the vinyl polymer is polyvinyl acetate (PVA), which is notably prepared by radical polymerization of the vinyl acetate monomer and then hydrolysis. It is notably possible to use the polyvinyl acetate hydrolyzed to 88%, such as that sold under the name CELVOL® 540 PV ALCOHOL by the company Celanese Chemicals;

the film-forming cellulose derivatives, such as hydroxyethylcellulose, hydroxypropylcellulose, hydroxypropylmethylcellulose, methylcellulose, ethylhydroxyethylcellulose, carboxymethylcellulose, and the quaternized derivatives of cellulose. Preferably, the cellulose derivatives are selected from hydroxypropylcellulose (HPC) and hydroxypropylmethylcellulose (HPMC). These polymers are soluble in water and in organic solvents. This makes it possible to increase the solubility range of the films containing them. The molecular weight of these cellulose polymers must be chosen carefully to increase the dissolution of the films. The HPCs preferably used are those marketed by the company Hercules under the name—Klucel® MF with molecular weight of 850 000 (viscosity 4000-6500 mPa at 2% in water)—Klucel® EF with molecular weight of 80 000 (viscosity 300-600 mPa at 10% in water). The HPMC preferably used is hydroxypropylmethylcellulose of viscosity 40-60 cP (40-60 mPa) at 2% in water at 20° C., marketed by the company Sigma-Aldrich.

starches and derivatives thereof;

polymers of natural origin, optionally modified, such as pullulan, pectin, mannan, the galactomannans, the glucomannans and derivatives thereof, gum arabic, guar gum, xanthan gum, karaya gum, the alginates, the carrageenans, the ulvans and other algal colloids, hyaluronic acid and derivatives thereof, shellac, sandarac gum, the dammars, elemis, copals, deoxyribonucleic acid, the mucopolysaccharides such as hyaluronic acid, chondroitin sulfate;

the anionic, cationic, amphoteric or nonionic polymers derived from chitin or chitosan;

the protein polymers, such as wheat or soya proteins; keratin and derivatives thereof, for example the keratin hydrolyzates and the sulfonic keratins, casein, albumin, collagen, glutelin, glucagon, gluten, zein, the gelatins and derivatives thereof;

the acrylic copolymers of phosphoryl choline, such as poly-2-(methacryloyloxyethyl)phosphorylcholine marketed under the name Lipidure® HM by the company NOF Corporation (INCI name: Polyphosphorylcholine glycol acrylate);

the anion-cation complexes of the gum arabic/gelatin or gum arabic/chitosan, or collagen/GlycosAminoGlycan type;

and mixtures of these polymers.

According to a preferred embodiment of the invention, the film-forming polymer is selected from the vinyl polymers, the cellulose derivatives and mixtures thereof.

Preferably, the film-forming polymer is selected from polyvinyl acetate, hydroxypropylcellulose, hydroxypropylmethylcellulose, and mixtures thereof, the polyurethanes, the nitrocelluloses, and the carbomers.

In particular, the composition according to the invention comprises one or more film-forming polymer(s) at a content ranging from 10 to 95 wt %, preferably from 20 to 70 wt %, and more preferably from 30 to 60 wt %, relative to the total weight of the film.

When it is in the form of anhydrous film, the composition according to the invention can comprise at least one organic solvent, which can be selected from:

ketones such as methyl ethyl ketone, methyl isobutyl ketone, diisobutyl ketone, isophorone, cyclohexanone, acetone;

alcohols that are liquid at room temperature such as ethanol, isopropanol, diacetone alcohol, 2-butoxyethanol, cyclohexanol, n-propanol, n-butanol; ethers of propylene glycol that are liquid at room temperature such as monomethyl ether of propylene glycol, monomethyl ether acetate of propylene glycol, mono-n-butyl ether of dipropylene glycol;

glycols such as ethylene glycol, propylene glycol, pentylene glycol, glycerol cyclic ethers such as γ-butyrolactone;

short-chain esters (having from 3 to 8 carbon atoms in total) such as ethyl acetate, butyl acetate, methyl acetate, propyl acetate, isopropyl acetate, isopentyl acetate, methoxypropyl acetate, butyl lactate;

ethers such as diethyl ether, dimethyl ether or dichlorodiethyl ether;

alkanes that are liquid at room temperature such as decane, heptane, dodecane, cyclohexane;

alkyl sulfoxides such as dimethylsulfoxide;

aldehydes that are liquid at room temperature such as benzaldehyde, acetaldehyde;

ethyl 3-ethoxypropionate;

carbonates such as propylene carbonate, dimethyl carbonate, acetals such as methylal;

and mixtures thereof.

According to a preferred embodiment, the organic solvent is volatile.

"Volatile organic solvent" means an organic solvent liable to evaporate in contact with the skin in less than one hour, at room temperature and atmospheric pressure. The volatile organic solvent is liquid at room temperature, notably has a non-zero vapour pressure at room temperature and atmospheric pressure, in particular it has a vapour pressure ranging from 0.13 Pa to 40 000 Pa (10<-3> at 300 mmHg), and preferably ranging from 1.3 Pa to 8000 Pa (0.01 to 60 mmHg).

According to a particularly preferred embodiment, the organic solvent is selected from the alcohols that are liquid at room temperature such as ethanol, isopropanol, diacetone alcohol, 2-butoxyethanol, cyclohexanol and mixtures thereof, and preferably ethanol and/or the short-chain esters (having from 3 to 8 carbon atoms in total) such as ethyl acetate, butyl acetate, methyl acetate, propyl acetate, isopropyl acetate, isopentyl acetate, methoxypropyl acetate, butyl lactate.

According to a more preferred embodiment, the organic solvent used in the compositions according to the invention is selected from ethanol, ethyl acetate or a mixture thereof.

The organic solvent can represent from 60 to 95 wt %, preferably from 65 to 85 wt %, and preferably from 65 to 80 wt %, relative to the total weight of the composition.

In the composition of the invention it is also possible to use a polymer that is both a film-forming polymer and a thickening polymer, selected for example from the cellulose derivatives and the polymers of natural origin that can be both film-forming and thickening.

According to a particular embodiment, the composition according to the invention, when it is in the form of a film, comprises, besides the film-forming polymer, at least one polysaccharide thickener.

The polysaccharide thickeners used in the film according to the invention can be selected from the polysaccharides with gelling capacity.

The definition of "gelling capacity" is that at a concentration greater than or equal to 0.5 wt % in water, the viscosity of the solutions thus obtained is greater than or equal to 0.01 Pa·s for a shear rate equal to 1, the measurements being performed at 25° C. using a RheoStress R5150 rheometer from Haake in cone-plate configuration, the measuring cone having the following dimensions: diameter: 60 mm and angle: 2°.

The polysaccharide thickeners can notably be selected from gum arabic, ghatti gum, karaya gum, carob gum, guar gum, tamarind gum, xanthan gum, gellan, the pectins, tragacanth, agar, the alginates, carrageenan, furcelleran, konjac and the cellulose derivatives, and mixtures thereof.

According to a preferred embodiment of the invention, the polysaccharide thickeners are selected from the carrageenans, which are linear polysaccharides extracted from certain red algae of the Rhodophyceae family. They consist of alternating α-1,3 and β-1,4 galactose residues, and numerous galactose residues can be sulfated.

There are three types of carrageenans, called Kappa-carrageenan, Iota-carrageenan and Lambda-carrageenan. This family of polysaccharides is described for example in chapter 3 of the book "Food Gels" edited by Peter HARRIS, Elsevier 1989. It is possible in particular to use the carrageenan sold under the name SATIAGUM® UTC 10 by the company Degussa.

The amount of thickener(s) in the composition according to the invention can range for example from 0.5 to 40 wt %, in particular from 1 to 20 wt %, and more particularly from 5 to 10 wt % relative to its total weight.

Moreover, according to an advantageous embodiment, the composition in the form of a film can incorporate, together with the polymer as defined above, at least one alkoxylated polydimethylsiloxane derivative.

As described in document FR0653343, said derivative has the advantage of significantly increasing the dissolution kinetics of the water-soluble film in which it is incorporated.

The alkoxylated polydimethylsiloxanes (PDMS) used according to the invention are water-soluble or water-dispersible.

"Water-soluble or water-dispersible" means PDMS having a solubility in water measured at 25° C. at least equal to 0.1 g/L (obtaining a solution macroscopically isotropic and transparent, colored or not). This solubility is preferably greater than or equal to 1 g/l.

These PDMS are preferably selected from the water-soluble silicones having at least one monovalent polyalkoxylated group, terminal or pendant, and which, introduced at 0.05 wt % in an aqueous solution, are able to reduce the surface tension of water to a value below 35 mN/m, and preferably below 30 mN/m.

Alkoxylated PDMS of this kind are for example sold by the company OSI under the trade names Silwet, Silwet 1614, and Tegowet.

According to a particularly preferred embodiment, the composition according to the invention is in the form of an anhydrous water-soluble film comprising (i) at least one synthetic polysulfated oligosaccharide, (ii) at least one water-soluble or water-dispersible film-forming polymer and (iii) at least one alkoxylated polydimethylsiloxane derivative.

The composition according to the invention, notably when it is in the form of a film, can further comprise one or more plasticizers selected for example from castor oil, or the polyols such as glycerin, sorbitol, the mono- and/or disaccharides, dipropylene glycol, butylene glycol, pentylene glycol, the polyethylene glycols such as PEG-400.

The amount of plasticizer(s) can range for example from 1 to 40 wt % and preferably from 2 to 15 wt % relative to the total weight of the composition.

Method of Cosmetic Treatment

According to another aspect, the invention relates to a method of cosmetic treatment using the compositions according to the invention.

Preferably, the invention relates to a method of cosmetic treatment of stretch marks using said compositions.

Method of cosmetic treatment means, in the sense of the present invention, a nontherapeutic method, in particular a method whose benefit is essentially visual and aesthetic.

The method of cosmetic treatment of the invention can be carried out notably by applying the cosmetic and/or dermatological compositions or combinations as defined above, according to the usual technique for using these compositions. For example: applications of creams, gels, water-soluble polymer film of the filmogel® type, serums, lotions, milks for makeup removal or after-sun compositions.

The cosmetic procedure according to the invention can be carried out by topical administration, daily for example, of the combination according to the invention, which can for example be formulated in the form of gels, lotions, emulsions.

The method according to the invention can comprise a single administration. According to another embodiment, administration is repeated for example 2 to 3 times daily for one day or more and generally for a prolonged duration of at least 4 weeks, or even 4 to 15 weeks, with one or more periods of interruption if required.

Compositions According to the Invention

According to a preferred embodiment, the composition according to the invention is in the form of an oil-in-water emulsion, preferably in the form of cream, comprising:
- 0.1 to 5% of potassium salt of sucrose octasulfate KSOS
- 40 to 60 wt % of water,
- 20 to 40 wt % of at least one oil,
- 1 to 10 wt % of at least one surfactant,
- 0 to 10 wt % of at least one wax,
- 0 to 20 wt % of active substances,
- 0 to 2 wt % of preservatives,
- 0 to 5 wt % of thickeners.

According to another preferred embodiment, the composition according to the invention is in the form of a water-based filmogel composition comprising:
- 0.1 to 5% of potassium salt of sucrose octasulfate KSOS
- 70 to 99 wt % of water,
- 0 to 10 wt % of active substances,
- 0 to 2 wt % of preservatives,
- 0 to 5 wt % of thickeners.

According to yet another preferred embodiment, the composition according to the invention is in the form of a solvent-based filmogel composition comprising:
- 0.01 to 5% of potassium salt of sucrose octasulfate KSOS
- 15 to 50 wt % of ethanol,
- 40 to 60% of ethyl acetate,
- 5 to 20 wt % of film-forming polymer of the nitrocellulose type,
- 5 to 20 wt % of plasticizer, preferably castor oil,
- 0 to 2 wt % of preservatives,
- 0 to 5 wt % of thickeners.

Use of the Compositions of the Invention

The use according to the invention can be such that the compositions or combinations defined above are employed in a formulation intended for topical use.

In particular, the invention relates to a topical composition for treating stretch marks or wounds in a subject having a predisposition to the development of stretch marks comprising, in a physiologically acceptable vehicle, at least an effective amount of at least one synthetic polysulfated oligosaccharide having 1 to 4 monosaccharide units, salts and/or derivatives thereof.

According to another embodiment, the invention relates to a synthetic polysulfated oligosaccharide having 1 to 4 monosaccharide units, salts and/or derivatives thereof for treating or preventing stretch mark scars.

According to yet another embodiment, the invention relates to the use of a synthetic polysulfated oligosaccharide having 1 to 4 monosaccharide units, salts and/or derivatives thereof in a cosmetic composition for treating stretch marks.

According to yet another embodiment, the invention relates to the use of a synthetic polysulfated oligosaccharide having 1 to 4 monosaccharide units, salts and/or derivatives thereof for manufacturing a cosmetic or dermatological composition intended for treating or preventing stretch mark scars.

The examples given below are presented for purposes of illustration and do not limit the field of the invention.

EXAMPLES

Example 1

A formulation was prepared in the form of cream (oil-in-water emulsion) comprising a synthetic polysulfated oligosaccharide according to the invention having the following composition:

| Constituents | % |
| --- | --- |
| Oil-in-water surfactant | 5.000 |
| Emulsifying wax | 2.000 |
| Stearic acid | 1.000 |
| Isodecyl isononanoate | 6.000 |
| Silicone oil (Decamethyl-Cyclopentasiloxane) | 4.000 |
| Emollient ester (myristyl lactate) | 5.000 |
| Demineralized water | 62.100 |
| Thickener | 0.300 |
| Glycerin | 5.000 |
| Propylene glycol | 5.000 |
| Potassium salt of sucrose octasulfate KSOS | 0.500 |
| Preservative | 1.500 |
| NaOH 10% | 0.600 |
| Silicone surfactant | 2.000 |

The thickener was dispersed in the water. The glycerin, propylene glycol, KSOS and preservative were added, and homogenized. It was heated to 70-75° C. When the mixture reached 70-75° C., the water content was adjusted and then neutralized with 10% soda and the temperature was brought back up to 70-75° C.

At the same time, the oil-in-water surfactant, emulsifying wax, stearic acid, isodecyl isononanoate, silicone oil (Decamethyl-Cyclopentasiloxane), and emollient ester (myristyl lactate) were mixed together and heated to 70-75° C.

When the 2 mixtures reached 70-75° C., the second was added to the first while stirring vigorously, and it was stirred hot for 10 minutes.

Then the silicone surfactant was added and it was again stirred hot for 5 minutes.

Finally, the heating was stopped and it was left to cool to room temperature, maintaining sufficient stirring depending on the viscosity of the mixture. The mixture takes on an inhomogeneous appearance at around 35° C., but the cream then becomes smooth and shiny.

Example 2

A formulation of the solvent-based filmogel type was prepared, comprising a synthetic polysulfated oligosaccharide according to the invention having the following composition:

| Constituents | % |
| --- | --- |
| Nitrocellulose | 12.800 |
| Castor oil | 11.000 |
| Absolute ethanol | 24.90 |
| Ethyl acetate | 49.70 |
| UV filters | 1.500 |
| Potassium salt of sucrose octasulfate KSOS | 0.100 |

The nitrocellulose was diluted in a mixture of ethyl acetate and absolute ethanol. Then the castor oil, the UV filters and the KSOS were added until dissolved, obtaining a composition of the filmogel type.

Example 3

A formulation of the water-based filmogel type was prepared comprising a synthetic polysulfated oligosaccharide according to the invention having the following composition

| Constituents | % |
| --- | --- |
| Demineralized water | 93.200 |
| Thickener | 0.500 |
| Sorbitol | 2.000 |
| Dextran | 1.000 |
| Potassium salt of sucrose octasulfate KSOS | 1.000 |
| Methylparaben | 0.050 |
| Propylparaben | 0.050 |
| Phenoxyethanol | 0.700 |
| NaOH 10% | 1.500 |

The thickener was dispersed in the water while stirring vigorously, then the sorbitol and the dextran were added, heating to 40° C. to obtain better solubility.

The KSOS, the parabens and the phenoxyethanol were added, and stirred to homogenize. Then it was left to cool to room temperature by stopping the heating, adjusting the water loss if necessary. Finally, it was neutralized with soda and stirred for 10 minutes, before stopping the stirring.

The invention claimed is:

1. A method for treating stretch marks, comprising the administration to a subject in need thereof of a cosmetic and/or dermatological topical composition comprising in a physiologically acceptable vehicle, at least an effective amount of at least one of synthetic polysulfated oligosaccharide having 1 to 4 monosaccharide units, salts and/or complexes thereof.

2. The method as claimed in claim 1, wherein the composition comprises at least synthetic polysulfated oligosaccharide having 1 or 2 monosaccharide units selected from the pentoses and the hexoses, as well as the salts and/or complexes of these compounds.

3. The method as claimed in claim 1, wherein said synthetic polysulfated oligosaccharide having 1 or 2 monosaccharide units is selected from potassium salt of sucrose octasulfate, silver salt of sucrose octasulfate, the hydroxyaluminum complex of sucrose octasulfate and mixtures thereof.

4. The method as claimed in claim 1, wherein said synthetic polysulfated oligosaccharide is present at a content between 0.1 and 50 wt %, relative to the total weight of the composition.

5. The method as claimed in claim 1, wherein said synthetic polysulfated oligosaccharide is present in a content such that the amount salted-out on the stretch marks is between 0.001 g/l and 50 g/l.

6. The method as claimed in claim 1, wherein said synthetic polysulfated oligosaccharide is present in a content such that the amount salted-out on the stretch marks is between 0.01 and 10 g/l.

7. The method as claimed in claim 1, wherein the composition comprises one or more other active substance(s) selected from antibacterials, antiseptics, antifungals, anti-inflammatories, active substances promoting healing and/or restructuring of the skin, antipruritics, UV filters, soothing agents, hydrating agents, depigmenting agents, keratolytic agents, antivirals, analgesics, anesthetics, vitamins, and mixtures thereof.

8. The method as claimed in claim 7, wherein the active substance is selected from the active substances promoting healing and/or restructuring of the skin.

9. The method as claimed in claim 1, wherein the composition is in the form of solutions (aqueous, aqueous-alcoholic or oily), dispersions (lotion or serum type), emulsions of liquid or semiliquid consistency (milk type), suspensions or emulsions (cream type), aqueous or lipophilic gel, microemulsions, microcapsules, microparticles, vesicular dispersions of the ionic and/or nonionic type, nonabsorbent interface dressings.

10. The method as claimed in claim 1, wherein the composition is in the form of an oil-in-water emulsion cream, comprising:
    0.1 to 5% of potassium salt of sucrose octasulfate KSOS,
    40 to 60 wt % of water,
    20 to 40 wt % of at least one oil,
    1 to 10 wt % of at least one surfactant,
    0 to 10 wt % of at least one wax,
    0 to 20 wt % of active substances,
    0 to 2 wt % of preservatives,
    0 to 5 wt % of thickeners.

11. The method as claimed in claim 1, wherein the composition is in the form of a film.

12. The method as claimed in the claim 11, wherein it comprises one or more film-forming polymer(s) at a content ranging from 10 to 95 wt %, relative to the total weight of the film.

13. The method as claimed in the claim 11, wherein it comprises one or more film-forming polymer(s) at a content ranging from 20 to 70 wt %, relative to the total weight of the film.

14. The method as claimed in the claim 11, wherein it comprises one or more film-forming polymer(s) at a content ranging from 30 to 60 wt %, relative to the total weight of the film.

15. The method as claimed in claim 11, wherein the composition further comprises a polysaccharide thickener.

16. The method as claimed in claim 11, wherein the composition is in the form of an anhydrous water-soluble film comprising (i) at least one synthetic polysulfated oligosaccharide, (ii) at least one water-soluble or water-dispersible film-forming polymer and (iii) at least one alkoxylated polydimethylsiloxane.

17. The method as claimed in claim 11, wherein the composition is in the form of a solvent-based filmogel composition comprising:
    0.01 to 5% of potassium salt of sucrose octasulfate KSOS
    15 to 50 wt % of ethanol,
    40 to 60% of ethyl acetate, 5 to 20 wt % of film-forming polymer of the nitrocellulose type,
5 to 20% of plasticizer castor oil,
0 to 2 wt % of preservatives,
0 to 5 wt % of thickeners.

18. The method as claimed in claim 11, wherein the composition is in the form of a water-based filmogel composition comprising:
0.1 to 5% of potassium salt of sucrose octasulfate KSOS,
70 to 99 wt % of water,
0 to 10 wt % of active substances,
0 to 2 wt % of preservatives,
0 to 5 wt % of thickeners.

19. The method as claimed in claim 1, wherein the subject in need thereof is a woman.

20. The method as claimed in claim 1, wherein the subject in need thereof an obese subject.

21. The method as claimed in claim 1 wherein the composition is administered on the abdomen, the buttocks, the hips, the roots of the limbs, the breasts or the shoulders.

* * * * *